United States Patent [19]

Taylor et al.

[11] Patent Number: 4,871,743

[45] Date of Patent: Oct. 3, 1989

[54] L-GLUTAMIC ACID DERIVATIVES

[75] Inventors: Edward C. Taylor, Princeton, N.J.;
Philip M. Harrington, Plainwell,
Mich.; Chuan Shih, Indianapolis, Ind.

[73] Assignees: The Trustees of Princeton University,
Princeton, N.J.; **Eli Lilly and
Company,** Indianapolis, Ind.

[21] Appl. No.: 144,970

[22] Filed: Jan. 19, 1988

[51] Int. Cl.$^4$ .................. A61K 31/505; C07D 239/42;
C07D 239/49; C07D 239/50
[52] U.S. Cl. .................................... 514/272; 514/269;
514/275; 544/321; 544/325; 544/320; 544/323

[58] Field of Search ............... 544/321, 325, 320, 323;
514/269, 272, 275

[56] References Cited

U.S. PATENT DOCUMENTS 4,792,557 12/1988 Kompis et al. ...................... 514/275

*Primary Examiner*—John M. Ford
*Attorney, Agent, or Firm*—Mathews, Woodbridge, Goebel, Pugh & Collins

[57] ABSTRACT

Pyrimidin-5-yl derivatives of L-glutamic acid are antineoplastic agents. A typical embodiment is N-(4-[4-(2,4-diamino-6-hydroxypyrimidin-5-yl)-butyl]-benzoyl)-L-glutamic acid.

15 Claims, No Drawings

L-GLUTAMIC ACID DERIVATIVES

This invention pertains to derivatives of L-glutamic acid which are antineoplastic agents, to their preparation and use, and to intermediates useful in their preparation.

BACKGROUND OF THE INVENTION

The folic acid antimetabolites aminopterin and amethopterin (also known as 10-methylaminopterin or methotrexate) or antineoplastic agents. These compounds inhibit enzymatic conversions involving metabolic derivatives of folic acid. Amethopterin, for example, inhibits dihydrofolate reductase, an enzyme necessary for the regeneration of tetrahydrofolate from dihydrofolate which is formed during the conversion of 2-deoxyuridylate to thymidylate by the enzyme thymidylate synthetase.

Other derivatives of folic acid and aminopterin have been synthesized and tested as anti-metabolites. Among these are compounds in which a methylene or methylidene group occupies a position in the molecule normally occupied by an imino or nitrilo group, respectively. These derivatives have varying degrees of antimetabolic activity. 10-Deazaaminopterin is highly active (Sirotak et al., *Cancer Treat. Rep.*, 1978, 62, 1047) and 5-deazaaminopterin has activity similar to that of amethopterin (Taylor et al., *J. Org. Chem.*, 1983, 48, 4852). 8,10-Dideazaaminopterin is reported to be active (U.S. Pat. No. 4,460,591) and 5,8,10-trideazaaminopterin exhibits activity against mouse L1210 leukemia (Yan et al., *J. Heterocycl. Chem.*, 1979, 16, 541). 10-Deazafolic acid, on the other hand, shows no significant activity (Struck et al., *J. Med. Chem.*, 1971, 14, 693) and 5-deazafolic acid is only weakly cytotoxic. 8,10-Dideazafolic acid is only marginally effective as a dihydrofolate reductase inhibitor (De Graw et al., "Chemistry and Biology of Pteridines", Elsevier, 1979, 229) and 5,8,10-trideazafolic acid also shows only marginal activity against mouse L1210 leukemia (Oatis et al., *J. Med. Chem.*, 1977, 20, 1393). 5,10-Dideazaaminopterin and 5,10-dideaza-5,6,7,8-tetrahydroaminopterin, and the corresponding 5,10-dideazafolic acid derivatives are reported by Taylor et al., *J. Med. Chem.*, 28: 7, 914 (1985).

DISCLOSURE OF INVENTION

The invention pertains to glutamic acid derivatives of the formula:

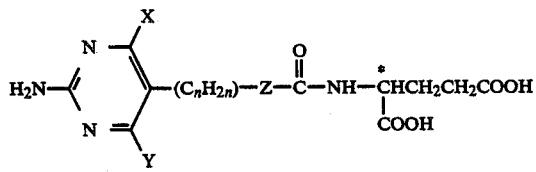

(I)

in which each of X and Y, independently of the other is hydroxy or amino;
Z is 1,4-phenylene, unsubstituted or substituted with one to four chlorine or fluorine atoms; cyclohexa-1,4-diyl; or a straight or branched chain alkylene group of 2 to 5 carbon atoms;
n has a value of 2 to 6;
the configuration about the carbon atom designated * is L; and the pharmaceutically acceptable salts thereof.

The invention also pertains to methods for the preparation of such compounds, to intermediates useful in those preparations, and to methods and compositions for the use of such compounds in combating neoplastic growth.

MODES FOR CARRYING OUT THE INVENTION

The compounds of Formula I exist in tautomeric equilibrium with the corresponding 4-oxo and 4-imino compounds:

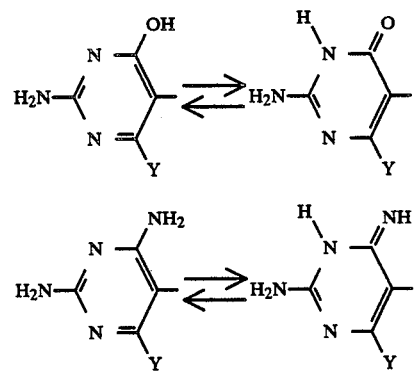

For convenience, the 3,4-dehydro-4-hydroxy and 3,4-dehydro-4-amino forms are depicted, and the corresponding nomenclature is used, throughout this specification, it being understood that in each case such includes the tautomeric 4(3H)-oxo and imino forms.

The subscript n can have a value of from 2 to 6, thereby denoting a divalent alkylene group of 2 to 6 carbon atoms, such as ethylene, trimethylene, 1,2-propylene, 2,3-propylene, tetramethylene, 1,2-butylene, 2,3-butylene, pentamethylene, 1,2-pentylene, 2,3-pentylene, 1,3-pentylene, hexamethylene, 1,2-hexylene, 2,3-hexylene, 2,4-hexylene and the like. Preferably n has a value of 3 to 5. Moreover, when n is 4 or 5, the two monovalent carbon atoms preferably are separated by two carbon atoms; i.e., tetramethylene, 1,4-pentylene, 2,5-pentylene, and pentamethylene. It will be appreciated that a given branched alkylene group such as 1,4-pentylene can be oriented in either of two ways—with the branched carbon atom adjacent to the pyrimidin-5-yl group or adjacent to Z.

The group Z is a hydrocarbon bridge which can be 1,4-phenylene which is unsubstituted or substituted with one to four chlorine or fluorine atoms; e.g., 2-chloro-1,4-phenylene, 2-fluoro-1,4-phenylene, 3-chloro-1,4-phenylene; 3-fluoro-1,4-phenylene; 2,6-dichloro-1,4-phenylene; 2,6-difluoro-1,4-phenylene; 3,5-dichloro-1,4-phenylene, 3,5-difluorophenylene, 2,3,5,6-tetrafluoro-1,4-phenylene, etc. Z also can be cyclopenta-1,4-diyl or an alkylene group of 2 to 5 carbon atoms; e.g., ethano, trimethylene, 1,3-butylene, 2,4-butylene, 1,3-pentylene, 2,4-pentylene or 3,5-pentylene.

Each of X and Y can be hydroxy or amino. Preferably Y is amino and most preferably Y is amino and X is hydroxy.

The invention includes the pharmaceutically acceptable alkali metal, alkaline earth metal, non-toxic metal, ammonium, and substituted ammonium salts, such as for example the sodium, potassium, lithium, calcium, magnesium, aluminum, zinc, ammonium, trimethylammonium, triethylammonium, triethanolammonium, pyridinium, substituted pyridinium, and the like.

The compounds can be prepared in a first process by hydrolysis of a 2-amino-pyrimidin-5-yl-L-glutamic acid derivative of the formula:

$$H_2N-\underset{\underset{Y}{\parallel}}{\overset{\overset{X}{\mid}}{\underset{N}{\overset{N}{\bigcirc}}}}-(C_nH_{2n})-Z-\overset{O}{\overset{\parallel}{C}}-NH-\underset{\underset{COOR^2}{\mid}}{CHCH_2CH_2COOR^3} \quad (II)$$

in which each of $R^2$ and $R^3$ is a carboxylic acid protecting group, and

X, Y, Z and n are as defined above.

Protecting groups encompassed by $R^2$ and $R^3$ and reactions for their removal are described, for example, in "Protective Groups in Organic Chemistry", Plenum Press, London and New York (1973); Greene, "Protective Groups in Organic Synthesis", Wiley, New York (1981); "The Peptides", Vol. I, Schröder and Lubke, Academic Press, London and New York (1965); in "Methoden der organischen Chemie", Houben-Weyl, 4th Edition, Vol. 15/I, Georg Thieme Verlag, Stuttgart (1974). Carboxylic acid protecting groups can be, for example, esters conceptually derived from lower alkanols of from 1 to 6 carbon atoms, including those branched in the 1-position and those which are substituted with one or more aromatic groups such as phenyl, or with halo or alkoxy; e.g., methyl, ethyl, t-butyl, benzyl, 4-nitrobenzyl, diphenylmethyl, methoxymethyl, and the like esters. Silyl esters such as trimethylsilyl also can be employed.

The hydrolysis is conducted at normal temperatures utilizing aqueous acid or base, such as for example, an aqueous alkali metal hydroxide, optionally in the presence of a water miscible organic solvent such as methanol, ethanol, tetrahydrofuran, dimethylformamide, and the like, or an acid, as for example trifluoroacetic acid. When base is used, the product is initially formed as the dicationic glutamate salt and can be readily precipitated by adjustment of pH, as through acidification with, for example, acetic acid. The resulting products generally are crystalline or microcrystalline solids.

Compounds of Formula II can be prepared by coupling a compound of the formula:

$$H_2N-\underset{\underset{Y}{\parallel}}{\overset{\overset{X}{\mid}}{\underset{N}{\overset{N}{\bigcirc}}}}-(C_{2n}H_{2n})-Z-\overset{O}{\overset{\parallel}{C}}OH \quad (III)$$

with a protected glutamic acid derivative of the formula:

$$R^2OCOCH\overset{*}{-}CH_2CH_2COOR^3 \quad (IV)$$
$$\underset{NH_2}{|}$$

utilizing a conventional condensation techniques for the formation of peptide bonds, such as activation of the carboxylic acid group through formation of a mixed anhydride, treatment with DCC, or the use of diphenylchlorophosphate.

Formation of the intermediate of Formula III can be accomplished by cyclization of an α-cyano dicarboxylate of the formula:

$$R^4CO-\underset{\underset{CN}{|}}{CH}-(C_nH_{2n})-Z-COR^{4'} \quad (V)$$

in which $R^4$ and $R^{4'}$ are the same or different alkoxy group of 1 to 6 carbon atoms and n and Z are as herein defined, with guanidine free base.

The intermediates of Formula V can be prepared by condensing an alkyl cyanoacetate of the formula:

$$R^4CO-CH_2-CN \quad (VI)$$

with a mesityl ester of the formula:

$$CH_3SO_2O-(C_nH_{2n})-Z-COR^{4'} \quad (VII)$$

in a strong base such as sodium hydride.

The mesityl ester intermediates of Formula VII can be obtained from hydroxy acid esters of the formula:

$$HO-(C_nH_{2n})-Z-COR^{4'} \quad (VIII)$$

which are either known or can be prepared by known methods, as more fully exemplified below.

Typical compounds of the present invention include:
N-(4-[3-(2,4-diamino-6-hydroxypyrimidin-5-yl)propyl]-benzoyl)-L-glutamic acid;
N-(4-[4-(2,4-diamino-6-hydroxypyrimidin-5-yl)butyl]-benzoyl)-L-glutamic acid;
N-(4-[2-chloro-4-(2,4-diamino-6-hydroxypyrimidin-5-yl)-butyl]benzoyl)-L-glutamic acid;
N-(4-[2-fluoro-4-(2,4-diamino-6-hydroxypyrimidin-5-yl)-butyl]benzoyl)-L-glutamic acid;
N-(4-[3-chloro-4-(2,4-diamino-6-hydroxypyrimidin-5-yl)-butyl]benzoyl)-L-glutamic acid;
N-(4-[3-fluoro-4-(2,4-diamino-6-hydroxypyrimidin-5-yl)-butyl]benzoyl)-L-glutamic acid;
N-(4-[2,6-difluoro-4-(2,4-diamino-6-hydroxypyrimidin-5-yl)butyl]benzoyl)-L-glutamic acid;
N-(4-[3,5-difluoro-4-(2,4-diamino-6-hydroxypyrimidin-5-yl)butyl]benzoyl)-L-glutamic acid;
N-(4-[5-(2,4-diamino-6-hydroxypyrimidin-5-yl)pentyl]-benzoyl)-L-glutamic acid;
N-(4-[3-(2,4,6-triaminopyrimidin-5-yl)propyl]-benzoyl)-L-glutamic acid;
N-(4-[4-(2,4,6-triaminopyrimidin-5-yl)butyl]-benzoyl)-L-glutamic acid;
N-(4-[5-(2,4,6-triaminopyrimidin-5-yl)pentyl]-benzoyl)-L-glutamic acid;
N-(4-[4-(2,4-diamino-6-hydroxypyrimidin-5-yl)propyl]-cyclohexylcarboxy)-L-glutamic acid;
N-[8-(2,4-diamino-6-hydroxypyrimidin-5-yl)-octanoyl]-L-glutamic acid;
N-[5-(2,4-diamino-6-hydroxypyrimidin-5-yl)-pentanoyl]-L-glutamic acid;
N-[6-(2,4-diamino-6-hydroxypyrimidin-5-yl)-hexanoyl]-L-glutamic acid;
N-[7-(2,4-diamino-6-hydroxypyrimidin-5-yl)-heptanoyl]-L-glutamic acid;
N-[9-(2,4-diamino-6-hydroxypyrimidin-5-yl)-nonanyl]-L-glutamic acid;

N-[10-(2,4-diamino-6-hydroxypyrimidin-5-yl)-
  decanoyl]-L-glutamic acid;
N-[11-(2,4-diamino-6-hydroxypyrimidin-5-yl)-
  undecanoyl]-L-glutamic acid; and
N-(4-[4-(2-amino-4,6-dihydroxypyrimidin-5-yl)butyl]-
  benzoyl)-L-glutamic acid.

The compounds of Formula I contain a chiral center in the L-glutamic acid portion of the molecule. The presence of one or more further chiral centers in either or both of —($C_nH_{2n}$)— or Z will lead to diastereomers. These diastereomers can be separated mechanically, as by chromatography, so that each is in a form substantially free of the other; i.e., having an optical purity of >95%. Alternatively, a mixture of diastereoisomeric compounds of Formula I is treated with a chiral acid operable to form a salt therewith. The resultant diastereoisomeric salts are then separated through one or more fractional crystallizations and thereafter the free base of the cationic moiety of at least one of the separated salts is liberated through treatment with a base and removal of the protecting groups. The liberation of the cationof the salt can be performed as a discrete step before or after the removal of the protecting groups, or concomitantly with the removal when such groups are susceptible to removal under basic conditions; i.e., basic hydrolysis.

Suitable chiral acids include the individual enantiomers of 10-camphorsulfonic acid, camphoric acid, alpha bromocamphoric acid, menthoxyacetic acid, tartaric acid, diacetyltartaric acid, malic acid, pyrrolidone-5-carboxylic acid, and the like.

The compounds of this invention have an effect on one or more enzymes which utilize folic acid, and in particular metabolic derivatives of folic acid, as a substrate.

The compounds of Formula I can be used, alone or in combination, to treat neoplasms including choriocarcinoma, leukemia, adenocarcinoma of the female breast, epidermid cancers of the head and neck, squamous or small-cell lung cancer, and various lymphosarcomas. In representative models for example, N-[4-(2,4-diamino-6-hydroxypyrimidin-5-butyl)benzoyl]-L-glutamic acid exhibited in IC$_{50}$ of 0.0632 mcg/ml against CCRF-CEM cell lines (a human T-cell derived leukemia). The compounds can also be used to treat mycosis fungoides, psoriasis, and arthritis.

The compounds may be administered either orally or preferably parenterally, alone or in combination with other anti-neoplastic agents, steroids, etc., to a mammal suffering from neoplasma and in need of treatment. Parenteral routes of administration include intramuscular, intrathecal, intravenous or intraarterial. In general, the compounds are administered in much the same fashion as methoxtrexate, but because of a different mode of action, can be administered in higher dosages than those usually employed with methoxtrexate. Dosage regimens must be titrated to the particular neoplasm, the condition of the patient, and the response but generally doses will be from about 10 to about 100 mg/day for 5-10 days or single daily administration of 250-500 mg, repeated periodically; e.g., every 14 days. Oral dosage forms include tablets and capsules containing from 1-10 mg of drug per unit dosage. Isotonic saline solutions containing 20-100 mg/ml can be used for parenteral administration.

The following examples will serve to further illustrate the invention.

EXAMPLE 1

To a mixture of 65.07 g (1.0 eq) of methyl 4-(4-hydroxybutyl)benzoate and 33.20 (1.05 eq) of triethylamine in 350 mL of anhydrous ethyl ether, stirred under nitrogen and cooled to 0° C., are added in a dropwise fashion, 37.58 g (1.05 eq) of mesityl chloride. A solid forms and the reaction mixture is gradually brought to room temperature and stirred under nitrogen for 4 hours. Four hundred milliliters of water are then added and the organic layer is separated, washed with water, dried over magnesium sulfate, and concentrated to yield methyl 4-(4-mesitylbutyl)benzoate, m.p. 52°–53° C.; IR (KBr) v$_{max}$ 3010, 2930, 2850, 1700, 1603, 1432, 1334, 1323, 1165, 1104, 937, 822, and 700 cm$^{-1}$; $^1$H NMR (CDCl$_3$) delta 7.92 (d, J=8.2 Hz, 2H, Ar), 7.22 (d, J=8.2 Hz, 2H, Ar), 4.18–4.22 (m, 2H, CH$_2$OMs), 3.86 (s, 3H OCH$_3$), 2.96 (s, 3H, SO$_2$CH$_3$), 2.65–2.68 (m, 2H, benzyl), 1.72–1.74 (m, 4H, 2° aliphatic).

Anal. Calcd. for C$_{13}$H$_{18}$SO$_5$: C, 54.53; H, 6.34; S, 11.20. Found: C, 54.79; H, 6.46; S, 11.17.

Methyl 4-(3-mesitylpropyl)benzoate, and methyl 4-(5-mesitylpentyl)benzoate and methyl 10-mesityldecanoate can be prepared in an analogous fashion.

EXAMPLE 2

A mixture of 10.30 g (1.1 eq) of 80% sodium hydride in mineral oil is washed twice with anhydrous tetrahydrofuran (to remove the mineral oil) and 400 mL of tetrahydrofuran are then added. This is cooled to 0° C. and a solution of 35.29 g (1.0 eq) of ethyl cyanoacetate in anhydrous tetrahydrofuran is added dropwise under nitrogen. The mixture is stirred vigorously at ambient temperatures until the evolution of hydrogen ceases and an anhydrous solution of 89.33 g (1.0 eq) of methyl 4-(4-mesitylbutyl)benzoate is then added in a dropwise fashion. The mixture is stirred at ambient temperatures for 12 hours, then at reflux temperatures for 6 hours, and then cooled. The solvent is removed under reduced pressure and diethyl ether is added. The organic phase is separated, washed with water and brine, dried over magnesium sulfate, filtered and concentrated. The residue is chromatographed with 1:4 ethyl acetate:hexane and the homogeneous fractions are combined and concentrated to yield methyl 4-(5-carboethoxy-5-cyanopentyl)benzoate as a liquid, IR (film) v$_{max}$ 2915, 2860, 2255, 1730, 1609, 1571, 1432, 1413, 1368, 1324, 1178, 1105, 1019, 962, 853, 759, and 602 cm$^{-1}$; $^1$H NMR (CDCl$_3$) delta 7.95 (d, J=8.1 Hz, 2H, Ar), 7.24 (d, J=8.1 Hz, 2H, Ar), 4.25 (q, J=7.2 Hz, 2H, CH$_2$CH$_3$), 3.90 (s, 3H, CO$_2$CH$_3$), 3.46 (t, J=6.8 Hz, 1H, CHCN), 2.69 (t, J=7.5 Hz, 2H, benzyl), 1.93–2.00 (m, 2H, CH$_2$CH), 1.54–1.72 (m, 4H, 2° aliphatic), 1.30 (t, J=7.3 Hz, 3H, CH$_2$CH$_3$).

Anal. Calcd. for C$_{17}$H$_{21}$NO$_4$: C, 67.31; H, 6.98; N, 4.62. Found: C, 67.10; H, 6.96; N, 4.33.

Methyl 4-(4-carbethoxy-4-cyanobutyl)benzoate, methyl 4-(4-carbethoxy-6-cyanohexyl)benzoate and methyl 11-carbethoxy-11-cyanoundecanoate can be prepared in an analogous fashion.

EXAMPLE 3

A mixture of 0.71 g (1.05 eq) of guanidine hydrochloride, 0.40 g (1.05 eq) of sodium methoxide, and 20 mL of anhydrous methanol is stirred under nitrogen for 30 minutes. The solid which forms is removed by filtration and the filtrate concentrated under reduced pressure. To the residue (guanidine free base) is added 2.15 g (1.0 eq) of methyl 4-(5-carbethoxy-5-cyanopentyl)benzoate in 20 mL of anhydrous dimethylformamide. This mixture is stirred under nitrogen with gentle heating for 12 hours, cooled, and then mixed with very dilute sulfuric acid. The solid is collected, washed with water and then diethyl ether, and dried to yield methyl 4-[4-(2,4-diamino-6-hydroxypyrimidin-5-yl)butyl]-benzoate, m.p. 203°-205° C.; IR (KBR) $v_{max}$ 3495, 3380, 2925, 2850, 1685, 1600, 1490, 1430, 1359, 1282, 1174, 1111, 1015, and 754 cm$^{-1}$; $^1$H NMR (d$^6$DMSO) delta 9.74 (bs, 1H (3)—NH), 7.83 (d, J=8.1 Hz, 2H, Ar), 7.31 (d, J=8.1 Hz, 2H, Ar), 5.87 (bs, 2H (2)—NH$_2$), 5.60 (bs, 2H (6)—NH$_2$), 3.80 (s, 3H, CH$_3$), 2.62 (t, J=7.6 Hz, 2H, (5)—CH$_2$), 2.15 (t, J=7.2 Hz, 2H, benzyl), 1.51-1.55 (m, 2H, 2° aliphatic), 1.26-1.28 (m, 2H 2° aliphatic).

Anal. Calcd. for C$_{16}$H$_{20}$N$_4$O$_3$: C, 60.75; H, 6.37; N, 17.71. Found: C, 61.05; H, 6.45; N, 17.46.

Methyl 4-[3-(2,4-diamino-6-hydroxypyrimidin-5-yl)propyl]benzoate, methyl 4-[5-(2,4-diamino-6-hydroxypyrimidin-5-yl)pentyl]benzoate and methyl 10-(2,4-diamino-6-hydroxypyrimidin-5-yl)decanoate can be prepared in a similar fashion.

EXAMPLE 4

A mixture of 0.91 g of methyl 4-[4-(2,4-diamino-6-hydroxypyrimidin-5-yl)butyl]benzoate and 40 mL of 1N sodium hydroxide is stirred with gentle heating for 18 hours and then filtered. Acidification with glacial acetic acid produces a solid which is collected by centrifugation with water. Upon concentration under reduced pressure, there is obtained 4-[4-(2,4-diamino-6-hydroyxpyrimidin-5-yl)butyl]benzoate acid, m.p. 293°-294° C.; IR (KBr) $v_{max}$ 3460, 3345, 3140, 2920, 2845, 1575, 1435, 1368, 1247, 1170, and 744 cm$^{-1}$; $^1$H NMR (d$^6$DMSO) delta 9.78 (bs, 1H (3)—NH), 7.80 (d, J=8.0 Hz, 2H, Ar), 7.26 (d, J=8.0 Hz, 2H, Ar), 5.88 (bs, 2H (2)—NH$_2$), 5.59 (bs, 2H, (6)—NH$_2$), 2.61 (t, J=7.4 Hz, 2H, (5)—CH$_2$), 2.15 (t, J=7.2 Hz, 2H, benzyl), 1.51-1.56 (m, 2H, 2° aliphatic), 1.27-1.31 L (m, 2H 2° aliphatic).

Anal. Calcd. for C$_{15}$H$_{18}$N$_4$O$_3$: C, 59.59; H, 6.00; N, 18.53. Found: C, 59.79; H, 5.77; N, 18.30.

4-[3-(2,4-diamino-6-hydroxypyrimidin-5-yl)-propyl]-benzoic acid, 4-[5-(2,4-diamino-6-hydroxypyrimidin-5-yl)pentyl]benzoic acid and 10-(2,4-diamino-6-hydroxypyrimidin-5yl)benzoic acid can be prepared in a similar fashion.

EXAMPLE 5

A mixture of 0.47 g (1.0 eq) of 4-[4-(2,4-diamino-6-hydroxypyrimidin-5-yl)butyl]benzoic acid, 0.62 g (1.5 eq) of phenyl N-phenylphosphoramidochloridate, 0.79 g (5.0 eq) of N-methylmorpholine, and 50 mL of anhydrous N-methylpyrrolidone is stirred under nitrogen at ambient temperatures for one hour. There is then added 0.75 g (2.0 eq) of diethyl L-glutamate hydrochloride and stirring is continued under nitrogen for 24 hours. The solvent is removed by vacuum distillation and chloroform was added to the residue. The chloroform solution is washed with water, dried over magnesium sulfate, filtered and concentrated under reduced pressure. The residue is chromatographed with 1:9 methanol:-chloroform to yield diethyl N-(4-[4-(2,4-diamino-6-hydroxypyrimidin-5-yl)butyl]benzoyl)-L-glutamate, m.p. 75°-76° C.; IR (KBr) $v_{max}$ 3320, 2920, 2915, 1845, 1720, 1580, 1529, 1427, 1368, 1326, 1192, 1093, 1021, 849 and 750 cm$^{-1}$; $^1$H NMR (CDCl$_3$) delta 11.58 (bs, 1H (3)—NH), 7.68 (d, J=7.9 Hz, 2H, Ar), 7.33 (d, J=7.9 Hz, 1H, NH), 7.17 (d, J=7.9 Hz, 2H, Ar), 5.54 (bs, 2H (2)—NH$_2$), 4.76-4.82 (m, 1H, CH), 4.71 (bs, 2H, (6)—NH$_2$), B 4.23 (q, J=7.11 Hz, 2H, CO$_2$CH$_2$), 4.12 (q, J=6.5 Hz, 2H, CO$_2$CH$_2$), 2.15-2.68 (m, 8H, 2° aliphatic) 1.57-1.66 (m, 2H, 2° aliphatic), 1.35-1.45 (m, 2H, 2° aliphatic), 1.30 (t, J=7.1 Hz, 3H, CH$_3$), 1.22 (t, J=7.1 Hz, 3H, CH$_3$); HRMS calcd for C$_{24}$H$_{33}$N$_5$O$_6$ (M+): 487.2430; found: 487.2415; other ions at m/e 348, 313, 285, 195, 167, 139, 97, and 84.

Anal. Calcd. for C$_{24}$H$_{33}$N$_5$O$_6$: C, 59.12; H, 6.82; N, 14.36. Found: C, 59.08; H, 6.79; N, 14.11.

Similarly prepared are diethyl N-(4-[3-(2,4-diamino-6-hydroxypyrimidin-5-yl)propyl]benzoyl)-L-glutamate, diethyl N-(4-[5-(2,4-diamino-6-hydroxypyrimidin-5-yl)pentyl]benzoyl)-L-glutamate; and diethyl N-[10-(2,4-diamino-6-hydroxypyrimidin-5-yl)decanoyl]-L-glutamate.

EXAMPLE 6

A mixture of 0.50 g of diethyl N-(4-[4-(2,4-diamino-6-hydroxypyrimidin-5-yl)butyl]benzoyl)-L-glutamate and 40 mL of 1N sodium hydroxide is stirred at room temperature for 72 hours. The mixture is neutralized with hydrochloric acid and the solid which forms is collected by filtration, washed with water and dried to yield N-(4-[4-(2,4-diamino-6-hydroxypyrimidin-5-yl)-butyl]benzoyl)-L-glutamic acid, m.p. 169°-171° C.; IR (KBr) $v_{max}$ 3340, 3200, 2920, 2860, 1600, 1380, 1170, and 755 cm$^{-1}$; $^1$H NMR (dTFA) delta 7.30 (d, J=8.7 Hz, 2H, Ar), 6.90 (d, J=8.7 Hz, 2H, Ar), 4.56-4.61 (m, 1H), 2.26-2.38 (m, 4H, 2' aliphatic), 1,93-2.14 (m, 4H, 2° aliphatic), 1.25-1.34 (m, 2H, 2° aliphatic), 1.05-1.17 (m, 2H, 2° aliphatic).

Similarly prepared are N-(4-[3-(2,4-diamino-6-hydroxypyrimidin-5-yl)propyl]benzoyl)-L-glutamic acid; N-(4-[5-(2,4-diamino-6-hydroxypyrimidin-5-yl)pentyl]-benzoyl)-L-glutamic acid; and N-[10-(2,4-diamino-6-hydroxypyrimidin-5yl)decanoyl]-L-glutamic acid.

EXAMPLE 7

The starting materials utilized in Example 1 are known or can be prepared by known procedures. The following procedures typify such preparations.

A. To a mixture of 0.082 g (0.005 eq) of palladium chloride, and 0.244 g (0.01 eq) of triphenylphosphine, and 20.0 g (1.0 eq) of methyl 4-bromobenzoate in diethylamine which is stirred under nitrogen is added 0.178 g (0.01 eq) of copper (I) iodide and 6.52 g (1.0 eq) of 3-butyn-1-ol. The reaction mixture is stirred under nitrogen at room temperature (about 25° C.) for eighteen hours. Diethylamine is then removed under reduced pressure, water is added, and the mixture extracted with benzene. The benzene extracts are filtered through silica to remove the metal residue and the filtrate concentrated under reduced pressure to yield methyl 4-(4-hydroxybuty-1-yn-1-yl)benzoate. Recrystallization from a mixture of benzene and hexane yields pure material in 75.8% yield, m.p. 95.5°-96.0° C.; IR (KBr) $v_{max}$ 3310, 2955, 1718, 1604, 1433, 1275, 1177, 1108, 1040, 955, 852, and 769 cm$^{-1}$; $^1$H NMR (CDCl$_3$) delta 7.98 (d, J=8.3 Hz, 2H, Ar), 7.49 (d, J=8.3 Hz, 2H, Ar), 3.93 (s, 3H, —CH$_3$), 3.87 (m, 2H, —CH$_2$OH), 2.74 (t, J=6.2 Hz, 2H, —yl—CH$_2$—), 1.88 (m, 1H, —OH).

Anal. Calcd. for C$_{12}$H$_{12}$O$_3$: C, 70.57; H, 5.92. Found: C, 70.36; H, 5.68.

By substituting 4-pentyn-1-ol for 3-butyn-1-ol, there is similarly obtained methyl 4-(5-hydroxypent-1-yn-1- yl)benzoate in 83% yield, m.p. 68.5°–69.5° C.; IR (KBr) $v_{max}$ 3360, 2955, 2855, 2220, 1720, 1604, 1431, 1405, 1307, 1272, 1193, 1172, 1112, 1063, 1017, 963, 904, 859, 769, and 696 cm$^{-1}$; $^1$H NMR (CDCl$_3$) delta 7.96 (d, J=8.3 Hz, 2H, Ar), 7.45 (d, J=8.3 Hz, 2H, Ar), 3.92 (s, 3H, —CH$_3$), 3.80–3.87 (m, 2H, —CH$_2$OH), 2.58 (t, J=7.0 Hz, 2H, yl—CH$_2$), 1.63 (bs, 1H, —OH).

Anal. Calcd. for C$_{13}$H$_{14}$O$_3$: C, 71.54; H, 6.47. Found: C, 71.26; H, 6.38.

B. A mixture of 2.55 g of methyl 4-(4-hydroxbut-1-yn-1-yl)benzoate in 200 mL of ethanol is hydrogenated at 50 psi for 12 hours in the presence of 0.26 g (10% weight equivalent) of 5% palladium on charcoal. The reaction mixture is filtered through a silica gel pad, which is washed with ethanol and concentrated to yield methyl 4-(4-hydroxybutyl)benzoate as an oil. IR (film) $v_{max}$ 3390, 2965, 2920, 2850, 1705, 1605, 1568, 1520, 1500, 1410, 1387, 1362, 1308, 1286, 1250, 1160, 1055, 1013, 843, 755, and 695 cm$^{-1}$; $^1$H NMR (CDCl$_3$) delta 7.95 (d, J=8.1 Hz, 2H, Ar), 7.25 (d, J=8.1 Hz, 2H, Ar), 3.89 (s, 3H, —CH$_3$), 3.65 L (t, J=6.3 Hz, 2H, —CH$_2$OH), 2.69 (t, J=7.5 Hz, 2H, benzyl), 1.66 (m, 4H, 2° aliphatic).

Anal. Calcd. for C$_{12}$H$_{16}$O$_3$: C, 69.21; H, 7.74. Found: C, 68.97; H, 7.92.

Similarly prepared is methyl 4-(5-hydroxypentyl)benzoate, IR (film) $v_{max}$ 3380, 2905, 2835, 1700, 1598, 1562, 1424, 1405, 1300, 1266, 1168, 1097, 1058, 1036, 1010, 953, 834, 747, and 692 cm$^{-1}$; $^1$H NMR (CDCl3) delta 7.94 (d, J=8.1 Hz, 2H, Ar), 7.23 (s, J=8.1 Hz, 2H, Ar), 3.89 (s, 3H, —CH$_3$), 3.62 (t, J=6.5 Hz, 2H, —CH$_2$OH), 2.66 (t, J=7.7 Hz, 2H, benzyl), 1.86 (bs, 1H, OH), 1.53–1.71 (m, 4H, 2° aliphatic), 1.35–1.45 (m, 2H, 2° aliphatic).

Anal. Calcd. for C$_{13}$H$_{18}$O$_3$: C, 70.25; H, 8.16. Found: C, 70.05; H, 8.17.

What is claimed is:

1. A compound of the formula:

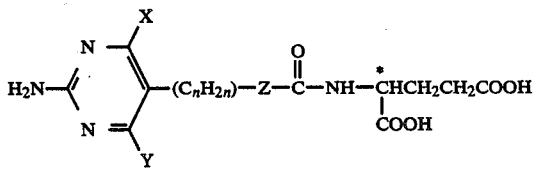

in which each X and Y, independently of the other is hydroxy or amino;
Z is 1,4-phenylene unsubstituted or substituted with one to four chlorine or fluorine atoms; cyclohexa-1,4-diyl; or a straight or branched chain alkylene group of 2 to 5 carbon atoms;
n has a value of 2 to 6; and
the configuration about the carbon atom designated * is L; and the pharmaceutically acceptable salts thereof.

2. A compound according to claim 1 in which Y is amino and X is hydrogen.

3. A compound according to claim 1 in which both X and Y are hydroxy.

4. A compound according to claim 1 in which both X and Y are amino.

5. A compound according to claim 1 in which Z is 1,4-phenylene, cyclohexa-1,4-diyl; or tetramethylene.

6. A compound according to claim 2 in which Z is 1,4-phenylene.

7. A compound according to claim 2 in which Z is cyclohexa-1,4-diyl.

8. A compound according to claim 4 in which Z is tetramethylene.

9. A compound according to claim 1 in which —(C$_n$H$_{2n}$)— is tetramethylene.

10. The method of combating neoplastic growth in a mammal which comprises administering to the mammal in a single or multiple dose regimen an effective amount of a compound according to claim 1.

11. A pharmaceutical composition for combating neoplastic growth in a mammal which comprises an amount of a compound according to claim 1 which upon administration to the mammal in a single or multiple dose regimen is effective to combat said growth, in combination with a pharmaceutically acceptable carrier.

12. A compound according to claim 1 which has the formula:

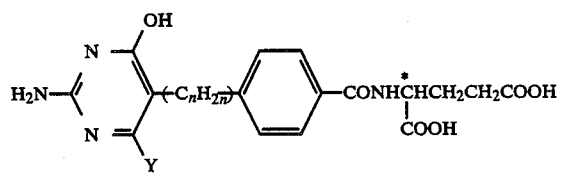

in which n has a value of 3 to 5 and the configuration about the carbon atom designated * is L.

13. The compound according to claim 12 which is N-(4-[4-(2,4-diamino-6-hydroxypyrimidin-5-yl)butyl]-benzoyl)-L-glutamic acid.

14. The method of combating neoplastic growth in a mammal which comprises administering to the mammal in a single or multiple dose regimen an effective amount of a compound according to claim 12.

15. A pharmaceutical composition for combating neoplastic growth in a mammal which comprises an amount of a compound according to claim 12 which upon administration to the mammal in a single or multiple dose regimen is effective to combat said growth, in combination with a pharmaceutically acceptable carrier.

* * * * *